(12) United States Patent
Couturier et al.

(10) Patent No.: US 7,214,810 B2
(45) Date of Patent: May 8, 2007

(54) ALKOXYAMINES DERIVED FROM BETA-PHOSPHORYLATED NITROXIDES, AND USE THEREOF FOR PREPARING POLYMERIZED OR NON-POLYMERIZED MONO- OR POLYALKOXYAMINES

(75) Inventors: Jean-luc Couturier, Lyons (FR); Olivier Guerret, Mazerolles (FR); Denis Bertin, Plan de Cuques (FR); Didier Gigmes, Marseilles (FR); Sylvain Marque, Antraigues sur Volane (FR); Paul Tordo, Marseilles (FR); Pierre-emmanuel Dufils, Carry le Rouet (FR)

(73) Assignee: Arkema France, Puteaux (FR)

( * ) Notice: Subject to any disclaimer, the term of this patent is extended or adjusted under 35 U.S.C. 154(b) by 244 days.

(21) Appl. No.: 10/813,822

(22) Filed: Mar. 31, 2004

(65) Prior Publication Data
US 2005/0065119 A1    Mar. 24, 2005

(30) Foreign Application Priority Data
Apr. 1, 2003    (FR) .................................... 03.03999

(51) Int. Cl.
*C07F 9/02*    (2006.01)
(52) U.S. Cl. .................. 558/87; 558/156; 558/177
(58) Field of Classification Search ............... 558/87, 558/156, 177
See application file for complete search history.

(56) References Cited
U.S. PATENT DOCUMENTS
6,657,043 B1   12/2003 Guerret et al.

FOREIGN PATENT DOCUMENTS
WO    00 71501    11/2000

OTHER PUBLICATIONS
Bertin, D., et al., 31P NMR measurement of the homolysis rate constant of the C-ON bond of β-phosphorylated alkoxyamines, e-polymers 2003, No. 002, pp. 1-9.

*Primary Examiner*—Kamal A. Saeed
*Assistant Examiner*—Robert Shiao
(74) *Attorney, Agent, or Firm*—Steven D. Boyd

(57) ABSTRACT

The invention relates to the use of alkoxyamines of formula (I):

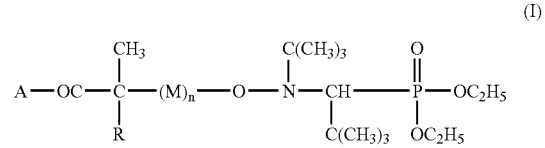

for the preparation of polymerized or non-polymerized mono- or polyalkoxyamines of formula (II):

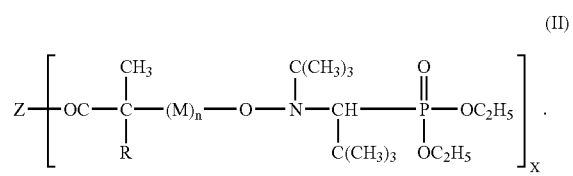

9 Claims, No Drawings

ALKOXYAMINES DERIVED FROM BETA-PHOSPHORYLATED NITROXIDES, AND USE THEREOF FOR PREPARING POLYMERIZED OR NON-POLYMERIZED MONO- OR POLYALKOXYAMINES

This application claims benefit, under U.S.C. §119(a) of French National Application Number 03.03999, filed Apr. 1, 2003.

SUMMARY OF THE INVENTION

The invention relates to the use of alkoxyamines derived from β-phosphorylated nitroxides of formula (I):

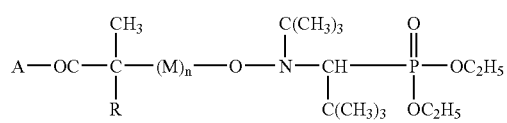

in which A represents a hydroxyl radical, a radical $R^1O-$ in which $R^1$ represents a linear or branched alkyl residue with a number of carbon atoms ranging from 1 to 6; a radical MeO— in which Me represents an alkali metal such as Li, Na or K, an $H_4N^+-$, $Bu_4N^+-$ or $Bu_3HN^+-$ radical; a chlorine atom; R represents a hydrogen atom or a methyl radical; M is a free-radical-polymerizable vinyl monomer sequence; n is an integer that may be equal to 0; for the preparation of polymerized or non-polymerized mono- or polyalkoxyamines, of formula (II):

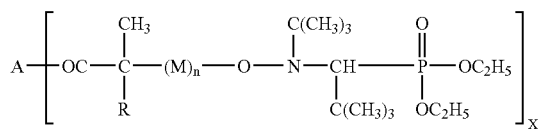

in which Z, which represents a mono- or polyfunctional structure, will be defined more fully later: x is an integer at least equal to one.

BACKGROUND OF THE INVENTION

European patent application EP 903 787 discloses alkoxyamines derived from β-phosphorylated nitroxides, which are used as free-radical polymerization initiators affording good polymerization control from (control of the masses, low polydispersities) in the case of numerous vinyl monomers: styrene and substituted styrenes, dienes, acrylic or methacrylic monomers, acrylonitrile.

The Applicant has found that reactive functions of ester type present on these alkoxyamines, and also derived functions such as an acid, acid salt or acid chloride function, allow chemical conversions to be performed easily either on the initial alkoxyamine or on the polymer derived from this alkoxyamine. The conversion of the initial alkoxyamine gives access to a novel alkoxyamine and allows the adaptation of the initiator to the intended application. In particular, this conversion may make it possible to synthesize polyalkoxyamines from a monoalkoxyamine. The conversion of the polymer derived from the alkoxyamine allows novel functional groups to be introduced or allows coupling reactions with another polymer. In particular, this conversion can give access to block copolymers involving blocks that are not available via free-radical polymerization.

SUMMARY OF THE INVENTION

One subject of the invention is thus the use of the alkoxyamines of formula (I):

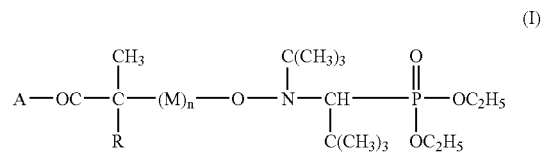

in which A represents a hydroxyl radical, a radical $R^1O-$ in which R1 represents a linear or branched alkyl residue containing a number of carbon atoms ranging from 1 to 6; a radical MeO— in which Me represents an alkali metal such as Li, Na or K; an $H_4N^+-$, $Bu_4N^+-$ or $Bu_3HN^+-$ radical; a chlorine atom; R represents a hydrogen atom or a methyl radical; M is a free-radical-polymerizable vinyl monomer sequence; n is an integer that may be equal to 0; for the preparation of polymerized or non-polymerized mono- or polyalkoxyamines, of formula (II):

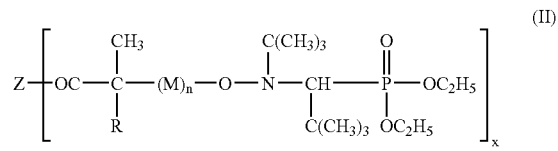

in which R and n have the same meaning as in formula (I); x is an integer at least equal to 1; Z represents a mono- or polyfunctional structure chosen from the structures given below in a non-limiting manner: $CH_2=CH-CH_2-O-$, $CH_2=CH-CH_2-NH-$, $CH_3-(OCH_2CH_2)p-O-$, $-O-(CH_2)q-O-$, p and q being integers at least equal to one, or more generally derived from compounds such as alcohols, polyols, amines, polyamines, epoxides, polyepoxides, esters, polyesters, amides, polyamides, imines, polyimines, polycarbonates, polyurethanes and silicones.

DETAILED DESCRIPTION OF THE INVENTION

As non-limiting examples of vinyl monomers M that may be used according to the present invention, mention will be made of styrene, substituted styrenes, dienes, acrylic monomers, for instance acrylic acid or alkyl acrylates, methacrylic monomers, for instance methacrylic acid or alkyl methacrylates, acrylonitrile, acrylamine and its derivatives, vinylpyrrolidinone or a mixture of at least two abovementioned monomers.

Alkoxyamines of formula (I) in which A represents a radical $R^1O-$ are known.

A subject of the invention is thus also the alkoxyamines of formula (I), with the exclusion of the alkoxyamines of formula (I) in which A represents a radical $R^1O-$.

The compounds (I) in which A is $OR^1$ may be obtained according to a method described in European patent application EP 903 787.

The compounds in which A is OH and n=0 may be prepared according to methods known in the literature. The most common method involves the coupling of a carbon radical with a nitroxide radical. The method involving the ATRA (Atom Transfer Radical Addition) reaction, as described in French patent application 2 791 979 incorporated into the present text by reference, may be used.

This method consists in reacting a nitroxide of formula (III):

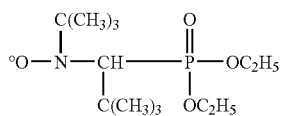

with a halogenated derivative of formula (IV):

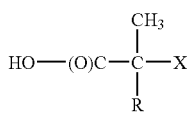

in which X represents a chlorine atom or a bromine atom, R having the same meaning as in formula (I), in water-immiscible organic solvent medium in the presence of an organometallic system of formula Metal Y(L)r, in which the Metal is copper, Y represents a chlorine atom or a bromine atom, L represents a ligand of the metal, and is chosen from polyamines such as:
tris[2-(dimethylamino)ethyl]amine:

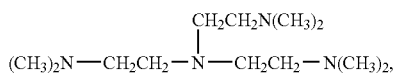

N,N,N',N',N''-pentamethyldiethylenetriamine (PMDETA):

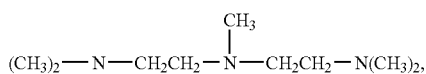

N,N,N',N'-tetramethylethylenediamine:

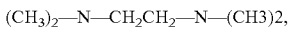

1,1,4,7,10,10-hexamethyltriethylenetetramine (HMTETA):

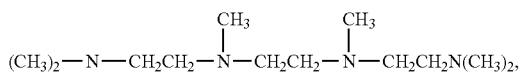

cyclic polyamines such as:
1,4,7-trimethyl-1,4,7-triazacyclononane,
1,5,9-trimethyl-1,5,9-triazacyclododecane,
1,4,8,11-tetramethyl-1,4,8,11-tetraazacyclotetradecane, by mixing together with stirring in the organic solvent a metal salt Metal-Y, the ligand L, the halogenated derivative (IV) and the nitroxide (III) in a (IV)/(III) molar ratio ranging from 1 to 1.4, and keeping the reaction medium stirred at a temperature of between 0° C. and 40° C. until the nitroxide (III) has completely disappeared, and then recovering the organic phase, which is washed with water, followed by isolating the alkoxyamine (I) by evaporating off the organic solvent under reduced pressure.

The organic solvent that will preferably be used is an aromatic hydrocarbon or a chlorinated derivative such as $CH_2Cl_2$.

The metal salt preferably used is CuBr.

CuBr (in which the copper is in oxidation state 1) and copper may also be introduced into the reaction medium.

The alkali metal salts of the alkoxyamines (I) (A=MeO—) may be readily obtained by dissolving, without heating, the alkoxyamine (I) in acid form in a minimum amount of methanol, followed by addition of 1.05 equivalents of alkali metal hydroxide in a minimum amount of water. The water/methanol mixture is evaporated off under reduced pressure and the remaining water is removed azeotropically with cyclohexane or benzene.

The compounds (I) in which A is Cl may be obtained by reacting compound (I) in which A is equal to OH with thionyl chloride.

The compounds (I) in which n=0 and R=H may be introduced as initiators-polymerization controllers to gain access to the compounds (I) in which n is other than 0.

The compounds of formula (II) may preferably be obtained via esterification, transesterification, amidation, transamidation and epoxide-opening reactions. It would not constitute a departure from the context of the invention if, for the esterification or amidation reactions, an intermediate acid chloride was used.

The esterification processes may in particular be used advantageously to prepare polyalkoxyamines from monoalkoxyamines.

The esterification and amidation processes may also be used advantageously to condense polymers that are not obtained via free-radical polymerization, for instance polyesters, polyamides or polyepoxides. These reactions thus allow access to a multitude of block copolymer structures, for instance polystyrene-polyester, polystyrene-polyamide, polystyrene-polyepoxide, polyacrylate-polyester, polyacrylate-polyamide or polyacrylate-polyepoxide.

By way of illustration, such reactions may be represented schematically as follows:

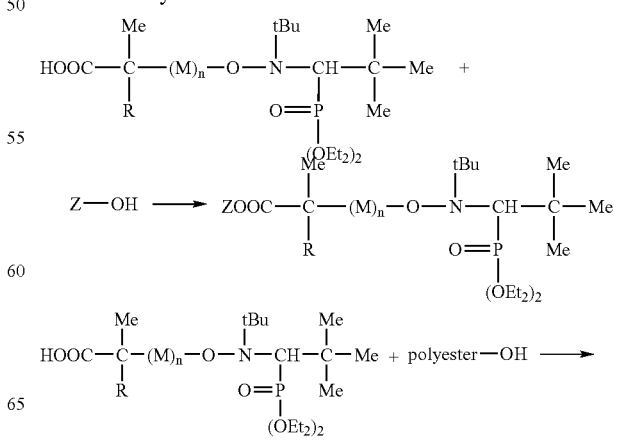

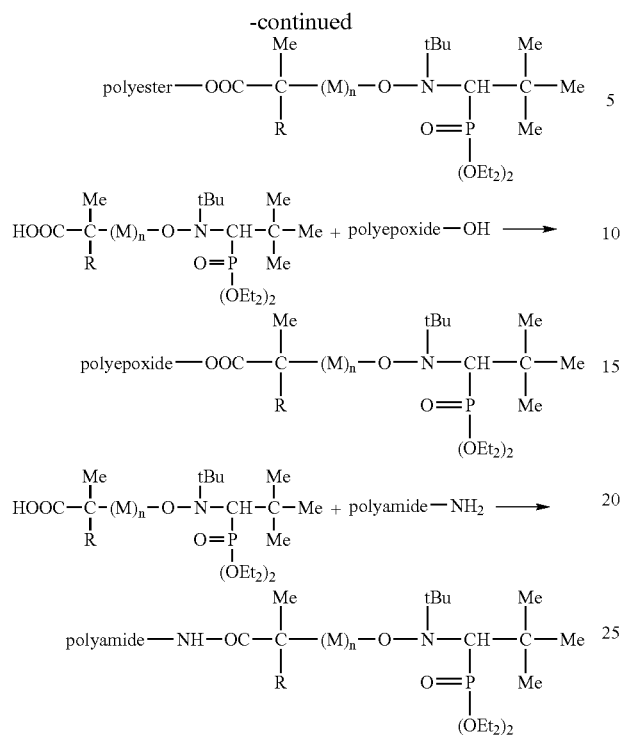

In general, to make a polymer reactive, a person skilled in the art generally uses either a free-radical grafting technique or a technique involving a functional initiator, for example of azo type. These techniques are not entirely satisfactory. The first method leads to a random distribution of the reactive functions on the chains. The second is limited by the initiation efficacy of the initiator used (which is not equal to 1) and by the fact that the initiated chains may become terminated by coupling or transfer (which gives rise to chains bearing 0, 1 or 2 functionalities).

The invention thus has in particular the advantage of producing and of using polymers whose chain-end functionality is fully controlled.

EXAMPLES

The examples that follow illustrate the invention in a non-limiting manner.

Example 1

Preparation of 2-[N-tert-butyl-N-(1-diethoxyphosphoryl-2,2-dimethylpropyl)aminoxy]propionic acid, referred to hereinbelow as AA-SG1 by hydrolysis of N-tert-butyl-N-1-diethylphophono-2,2-dimethylpropyl-O-1-methoxycarbonylethylhydroxylamine, referred to hereinbelow as MONAMS according to the reaction:

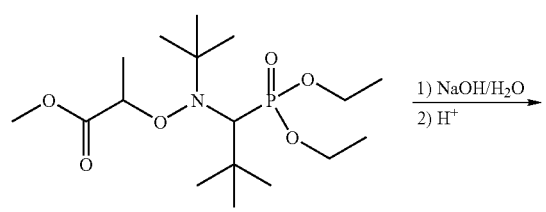

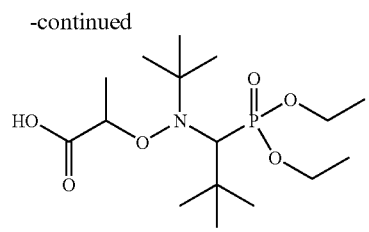

MONAMS is prepared according to European patent application EP 903 787.

3 g of MONAMS (7.9 mmol) dissolved in 45 ml of methanol are placed in a 100 ml round-bottomed flask. 0.4 g of sodium hydroxide (10 mmol) dissolved in 30 ml of water is added. The mixture is left to react at 50° C. for 24 hours. The reaction mixture is extracted with ether. The resulting aqueous phase is acidified to pH=2 with 5N HCl and then extracted with dichloromethane. The organic phase is evaporated under vacuum to give 2.6 g of the acid form of the alkoxyamine referred to as AA-SG1 in the form of a white powder (yield=90%).

Characterization of 2-[N-tert-butyl-N-(1-diethoxyphosphoryl-2,2-dimethylpropyl)-aminoxy]propionic acid:

m.p.=145° C. $^{31}$P NMR (121.59 MHz, CDCl$_3$):☐ 27.65 (s, Dia I, 65%). 24.60 (s, Dia II, 35%). $^1$H NMR (300 MHz, CDCl$_3$): Dia I. ☐ 4.68 (q, J=6 Hz, 1H), 3.90–4.35 (m, 4H), 3.38 (d, J=27 Hz, 1H), 1.61 (d, J=6 Hz, 3H), 1.34 (m, 6H), 1.20 (s, 9H), 1.19 (s, 9H). Dia II. ☐ 4.54 (q, J=9 Hz, 1H), 3.90–4.35 (m, 4H), 3.38 (d, J=27 Hz, 1H), 1.49 (d, J=9 Hz, 3H), 1.31 (t, J=9 Hz, 6H), 1.17 (s, 9H), 1.12 (s, 9H).

$^{13}$C NMR (75.54 MHz, CDCl$_3$): Dia I. ☐ 174.17 (s, $\underline{C}$OOH), 81.46 (s, $\underline{C}$H—O), 68.12 (d, J=139 Hz, $\underline{C}$H—P), 62.53 (s, N—$\underline{C}$(CH$_3$)$_3$), 62.65 (d, J=5.28 Hz, CH$_2$), 59.86 (d, J=7.55 Hz, CH$_2$), 35.54 (d, J=4.53 Hz, CH—$\underline{C}$(CH$_3$)$_3$), 30.24 (d, J=6.8 Hz, CH—C($\underline{C}$H$_3$)$_3$), 27.80 (s, N—C($\underline{C}$H$_3$)$_3$), 19.35 (s, CH—$\underline{C}$H$_3$), 16.31 (d, J=5.29 Hz, CH$_2$$\underline{C}$H$_3$), 16.04 (d, J=6.8 Hz, CH$_2$$\underline{C}$H$_3$). Dia II. ☐ 174.78 (s, $\underline{C}$OOH), 81.31 (s, $\underline{C}$H—O), 69.47 (d, J=141.26 Hz, $\underline{C}$H—P), 62.53 (s, N—$\underline{C}$(CH$_3$)$_3$), 62.22 (d, J=6.8 Hz, CH$_2$), 59.86 (d, J=7.55 Hz, CH$_2$), 35.59 (d, J=2.26 Hz, CH—$\underline{C}$(CH$_3$)$_3$), 29.85 (d, J=6.04 Hz, CH—C($\underline{C}$H$_3$)$_3$), 27.72 (s, N—C($\underline{C}$H$_3$)$_3$), 18.43 (s, CH—$\underline{C}$H$_3$), 16.35 (d, J=6.8 Hz, CH$_2$$\underline{C}$H$_3$), 16.13 (d, J=6.8 Hz, CH$_2$$\underline{C}$H$_3$).

Example 2

Esterification of AA-SG1

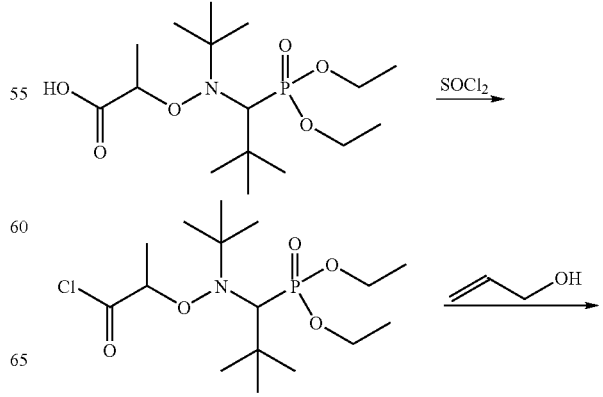

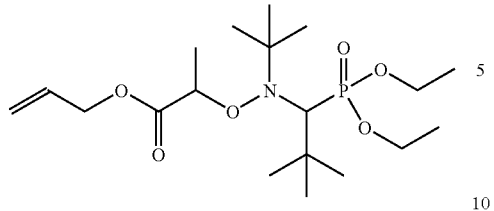

2 g of AA-SG1 (5.4 mmol) dissolved in 25 ml of dichloromethane predried over molecular sieves are placed in a 100 ml round-bottomed flask under a nitrogen atmosphere. 1.9 g of thionyl chloride (16.2 mmol) are added and the mixture is left to react for 45 minutes at room temperature. The reaction mixture is evaporated under vacuum to give the acid chloride of the alkoxyamine in the form of an oil, which is used in the subsequent synthesis without further purification.

The acid chloride obtained above is redissolved in 30 ml of ethyl ether (predried by distillation over sodium-benzophenone). A mixture containing 0.62 g of allyl alcohol (10.8 mmol), 0.55 g of triethylamine (5.4 mmol), 0.13 g of 4-dimethylaminopyridine (1.1 mmol) and 10 ml of ether is added thereto at room temperature. The mixture is left to react for 2 hours at room temperature. The reaction mixture is filtered, washed with aqueous 0.1 M HCl solution and then washed with aqueous 5% potassium bicarbonate solution. The organic phase is evaporated to give 1.53 g of the allylic amide of the alkoxyamine AA-SG1 (yield=60%).

Characterization of allyl 2-[N-tert-butyl-N-(1-diethoxnihosphoryl-2,2-dimethylpropyl)-aminoxy]propionate:

$^{31}$P NMR (121.59 MHz, CDCl$_3$): ☐ 23.23 (s, Dia I, 80%). 22.61 (s, Dia II, 20%). $^1$H NMR (300 MHz, CDCl$_3$): ☐ 5.96–5.87 (m, 2H, dia I+II), 5.37–5.23 (m, 4H, dia I+II), 4.64–4.58 (m, 6H, dia I+II), 4.25–3.93 (m, 8H, dia I+II), 3.37 (d, J=27 Hz, 1H, dia II), 3.27 (d, J=24 Hz, dia I), 1.53 (d, J=9 Hz, 3H, dia I), 1.50 (d, J=6 Hz, 3H, dia II), 1.36–1.27 (m, 12H, dia I+II), 1.17 (s, 9H, dia II), 1.16 (s, 9H, dia I), 1.14 (s, 9H, dia II), 1.11 (s, 9H, dia I). $^{13}$C NMR (75.54 MHz, CDCl3): Dia I. ☐ 173.43 (s, CO), 131.69 (s, CH=CH$_2$) 118.50 (s, CH=CH$_2$), 82.49 (s, CH—ON), 69.51 (d, J=139.75 Hz, CH—P), 64.90 (s, O—CH$_2$—CH), 61.71 (d, J=6.04 Hz, CH$_2$), 61.52 (s, N—C(CH$_3$)$_3$), 58.67 (d, J=7.55 Hz, CH$_2$), 35.45 (d, J=5.28 Hz, CH—C(CH$_3$)$_3$), 29.46 (d, J=5.28 Hz, CH—C(CH$_3$)$_3$), 27.81 (s, N—C(CH$_3$)$_3$), 19.19 (s, CH—CH$_3$), 16.40 (d, J=5.29 Hz, CH$_2$CH$_3$), 16.10 (d, J=6.8 Hz, CH$_2$CH$_3$). Dia II. ☐ 172.03 (s, CO), 132.06 (s, CH=CH$_2$), 117.97 (s, CH=CH$_2$), 82.49 (s, CH—ON).69.17 (d, J=139.75 Hz, CH—P), 64.83 (s, O—CH$_2$—CH), 61.81 (d, J=8.3 Hz, CH$_2$), 61.27 (s, N—C(CH$_3$)$_3$), 58.82 (d, J=6.8 Hz, CH$_2$), 35.10 (d, J=5.28 Hz, CH—C(CH$_3$)$_3$), 30.17 (d, J=6.04 Hz, CH—C(CH$_3$)$_3$), 27.87 (s, N—C(CH$_3$)$_3$), 17.73 (s, CH—CH$_3$), 15.80 (d, J=6.8 Hz, CH$_2$CH$_3$), 15.77 (d, J=6.8 Hz, CH$_2$CH$_3$).

Example 3

Amidation of AA-SG1

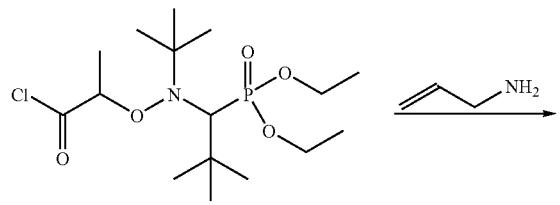

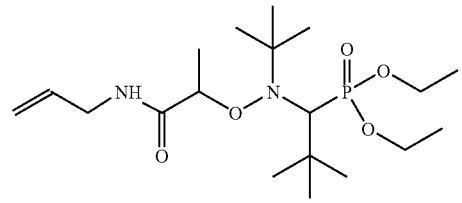

The acid chloride of the alkoxyamine AA-SG1 is synthesized in the same manner as in Example 2.

2.1 g of acid chloride (5.4 mmol) are dissolved in 30 ml of ethyl ether. A mixture containing 0.62 g of allylamine (10.8 mmol), 0.55 g of triethylamine (5.4 mmol), 0.13 g of 4-dimethylaminopyridine (1.1 mmol) and 10 ml of ether is added at room temperature. The mixture is left to react for two hours at room temperature. The reaction mixture is filtered, washed with aqueous 0.1 M HCl solution and then washed with aqueous 5% potassium bicarbonate solution. The organic phase is evaporated to give 1.53 g of the allylic amide of the alkoxyamine AA-SG1 (yield=70%).

Characterization of N-allyl-2-[N-tert-butyl-N-(1-diethoxyphosphoryl-2,2-dimethyl-propyl)aminoxy]propionamide:

$^{31}$P NMR (121.59 MHz, CDCl$_3$): ☐ 27.42 (s, Dia I, 35%). 27.05 (s, Dia II, 65%). $^1$H NMR (300 MHz, CDCl$_3$): Dia I ☐ 8.61 (b, NH, 1H), 5.96–5.83 (m, 1H), 5.19 (dq, J$_{HH}$=1.5 Hz, J$_{HH}$=18 Hz, 1H), 5.08 (dq, J$_{HH}$=1.5 Hz, J$_{HH}$=9 Hz, 1H), 4.48 (q, J=6 Hz, 1H), 4.29–3.97 (m, 5H), 3.67 (m, 1H), 3.35 (d, J=27 Hz), 1.51 (d, J=6 Hz, 3H), 1.35–1.28 (m, 6H), 1.21 (s, 9H), 1.08 (s, 9H). Dia II. 7.74 (b, NH, 1H), 5.96–5.83 (m, 1H), 5.21 (d, J=18 Hz, 1H), 205.11 (d, J=9 Hz, 1H), 4.51 (q, J=9 Hz, 1H), 4.20–3.95 (m, 5H), 3.88 (t, J=7.5 Hz, 1H), 3.28 (d, J=24 Hz), 1.63 (d, J=6 Hz, 3H), 1.36–1.28 (m, 6H), 1.25 (s, 9H), 1.24 (s, 9H). $^{13}$C NMR (75.54 MHz, CDCl$_3$): Dia I. ☐ 173.55 (s, CO), 134.40 (s, CH=CH$_2$) 115.18 (s, CH=CH$_2$), 81.76 (s, CH—ON), 68.56 (d, J=137.48 Hz, CH—P), 62.17 (s, N—C(CH$_3$)$_3$), 61.56 (d, J=6.04 Hz, CH$_2$), 59.64 (d, J=7.55 Hz, CH$_2$), 41.06 (s, N—CH$_2$), 35.36 (d, J=5.28 Hz, CH—C(CH$_3$)$_3$), 29.69 (d, J=6.04 Hz, CH—C(CH$_3$)$_3$), 28.15 (s, N—C(CH$_3$)$_3$), 19.21 (s, CH—CH$_3$), 16.25 (d, J=6.04 Hz, CH$_2$CH$_3$), 15.91 (d, J=6.8 Hz, CH$_2$CH$_3$). Dia II. ☐ 173.42 (s, CO), 134.27 (s, CH=CH$_2$), 116.30 (s, CH=CH$_2$), 83.05 (s, CH—ON), 69.25 (d, J=137.48 Hz, CH—P), 62.85 (s, N—C(CH$_3$)$_3$), 61.55 (d, J=6.04 Hz, CH$_2$), 60.04 (d, J=7.55 Hz, CH$_2$), 41.46 (s, N—CH$_2$), 35.33 (d, J=5.28 Hz, CH—C(CH$_3$)$_3$), 30.06 (d, J=5.28 Hz, CH—C(CH$_3$)$_3$), 28.38 (s, N—C(CH$_3$)$_3$), 19.55 (s, CH—CH$_3$), 16.55 (d, J=6.80 Hz, CH$_2$CH$_3$), 16.30 (d, J=6.8 Hz, CH$_2$CH$_3$).

Example 4

Preparation of the alkoxyamine 2-methyl-2[N-tert-butyl-N-(1-diethoxyphosphoryl-2,2-dimethylpropyl)aminoxy]propionic acid) referred to as methylpropionic acid-SG1

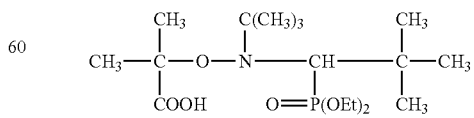

Procedure:

500 ml of degassed toluene, 35.9 g of CuBr (250 mmol), 15.9 g of copper powder (250 mmol) and 86.7 g of N,N, N',N',N''-pentamethyldiethylenetriamine-PMDETA-(500 mmol) are introduced into a 2 l glass reactor purged with nitrogen, followed by introduction, with stirring and at room temperature (20° C.), of a mixture (a solution) containing 500 ml of degassed toluene, 42.1 g of 2-bromo-2-methyl-propionic acid (250 mmol) and 78.9 g of 84% SG1, i.e. 225 mmol.

The mixture is left to react for 90 minutes at room temperature and with stirring, and the reaction medium is then filtered. The toluene filtrate is washed twice with 1.5 l of saturated aqueous $NH_4Cl$ solution.

A yellowish solid is obtained, which is washed with pentane to give 51 g of N-tert-butyl-N-1-diethylphosphono-2,2-dimethylpropyl-O-1-carboxymethylethylhydroxyl-amine (yield=60%).

The analytical results are given below:
molar mass determined by mass spectrometry: 381.44/g.mol$^{-1}$ (for $C_{17}H_{36}NO_6P$)
elemental analysis (empirical formula: $C_{17}H_{36}NO_6P$):
% calculated: C=53.53, H=9.51, N=3.67
% found: C=53.57, H=9.28, N=3.77
melting performed on Büchi B-540 apparatus: 124–125° C.

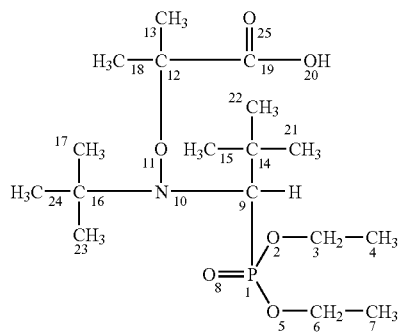

$^{31}P$ NMR (CDCl$_3$): δ 27.7

$^1H$ NMR (CDCl$_3$):

δ 1.15 (singlet, 9H on carbons 15, 21 and 22),

δ 1.24 (singlet, 9H on carbons 17, 23 and 24),

δ 1.33–1.36 (multiplet, 6H on carbons 4 and 7),

δ 1.61 (multiplet, 3H on carbon 18),

δ 1.78 (multiplet, 3H on carbon 13),

δ 3.41 (doublet, 1H on carbon 9),

δ 3.98–4.98 (multiplet, 4H on carbons 3 and 6)

δ 11.8 (singlet —OH).

$^{13}C$ NMR (CDCl$_3$):

| Carbon atoms No. | δ |
|---|---|
| 3 and 6 | 60.28–63.32 |
| 9 | 69.86 |
| 12 | 63 |
| 13 | 28.51 |
| 14 | 36.04 |
| 15, 21 and 22 | 29.75 |
| 16 | 63.31 |
| 17, 23 and 24 | 28.74 |
| 18 | 24.08 |
| 19 | 176.70 |

Example 5

Synthesis of a Dialkoxyamine from the Alkoxyamine Methylpropionic Acid-SG1

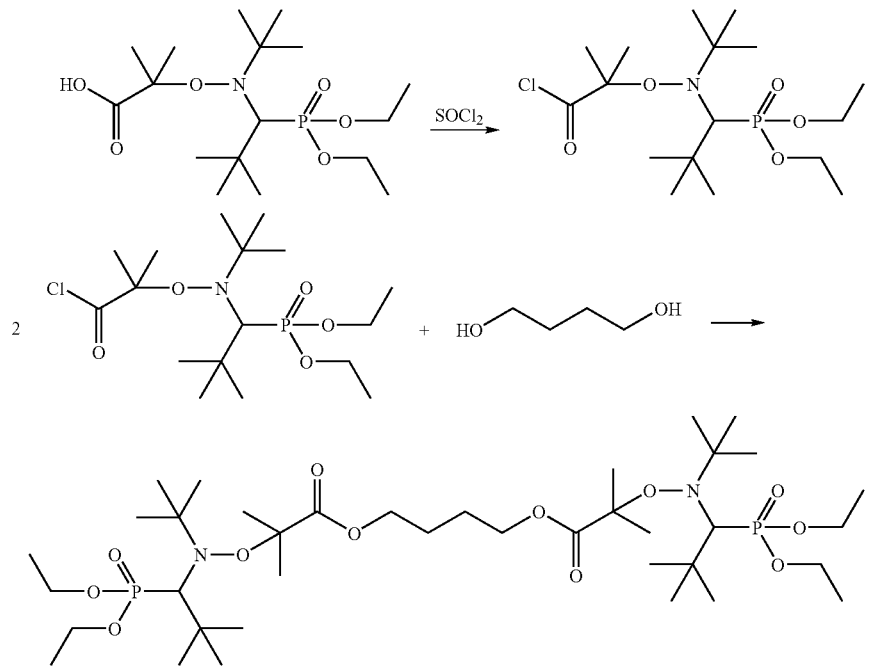

The alkoxyamine methylpropionic acid-SG1 is prepared according to Example 4.

10 g of alkoxyamine methylpropionic acid-SG1 (26 mmol) and 50 ml of dichloromethane (dried over calcium hydride) are introduced into a 250 ml reactor purged with nitrogen. 6.2 g of $SOCl_2$ (52 mmol) are added, via a dropping funnel, at room temperature. The mixture is left to react for 2 hours at room temperature with stirring and under a gentle stream of nitrogen. Evaporation under vacuum is performed to remove the excess $SOCl_2$ and the solvent. The acid chloride of the alkoxyamine is obtained, and is used in the subsequent synthesis without further purification.

The resulting oil is redissolved in 50 ml of dry dichloromethane. A mixture containing 1.2 g of 1,4-butanediol (13 mmol), 2.6 g of triethylamine (26 mmol) and 0.3 g of 4-dimethylaminopyridine (2.6 mmol) dissolved in 10 ml of dichloromethane is placed in the dropping funnel, under a nitrogen atmosphere. The above mixture is added dropwise to the reactor and the mixture is then left to react for three hours at room temperature. The reaction mixture is filtered, washed with a $KHCO_3$ solution and then washed with water. The organic phase is recovered, dried over magnesium sulphate and evaporated to dryness under vacuum at room temperature. A solid is obtained, which is washed with cold pentane to give 5.2 g of dialkoxyamine (yield=50%).

The dialkoxyamine was characterized by proton, carbon-13 and phosphorus NMR. $^{31}P$ NMR ($CDCl_3$): $\delta=26$ ppm.

Example 6

Coupling Between the Alkoxyamine Methylpropionic Acid-SG1 and a POE-Ome Block (Mn=750 g·mol$^{-1}$)

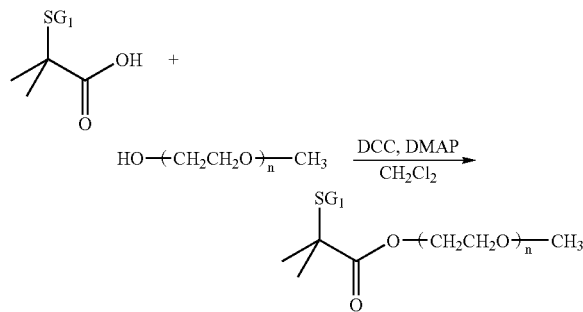

The alkoxyamine methylpropionic acid-SG1 (1 equivalent), the α-methoxylated poly(ethylene oxide) (1 equivalent) and 4-dimethylaminopyridine (DMAP) (1 equivalent) are placed in anhydrous dichloromethane in a round-bottomed flask equipped with a magnetic stirrer and a condenser. The solution is degassed by sparging with nitrogen for 10 to 15 minutes. Dicyclohexylcarbodiimide (DCC) (2.6 equivalents), dissolved in a minimum amount of dichloromethane, is added to the mixture via a syringe. The mixture is stirred for three hours at 0° C. The residual POE-OMe is removed by selective precipitation from ethanol. The filtrate is evaporated under vacuum. The degree of coupling, determined by proton NMR, is 37%.

What is claimed is:

1. A method for preparing a polymerised or non-polymerized mono- or polyalkoxyamine comprising reacting an alkoxyamine of formula (I):

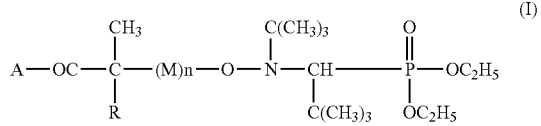

in which A represents a hydroxyl radical, a radical $R^1O$— in which $R^1$ represents a linear or branched alkyl residue containing a number of carbon atoms ranging from 1 to 6; a radical MeO— in which Me represents an alkali metal; an $H_4N^+$—, $BN_4N^+$— or $Bu_3HN^+$— radical; a chlorine atom; R represents a hydrogen atom or a methyl radical; M is a free-radical-polymerizable vinyl monomer sequence; n is an integer that may be equal to 0 or 1; to form a polymerised or nonpolymerized mono- or polyalkoxyamine of the formula (II):

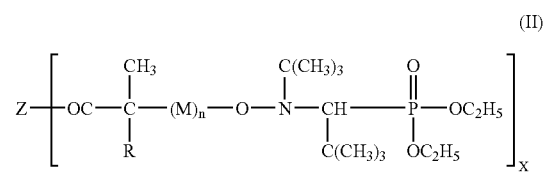

in which R and n have the same meaning as in formula (I); x is an integer equal to 1 or 2; Z represents a mono- or polyfunctional structure chosen from alcohols, polyols, amines, polyamines, epoxides, polyepoxides, esters, polyesters, amides, polyamides, imines, polyimines, polycarbonates, polyurethanes or silicones.

2. The method of claim 1 wherein said alkali metal Me is selected from the group consisting of Li, Na, K, and mixtures thereof.

3. The method of claim 1 in which M is styrene, substituted styrenes, dienes, acrylic monomers, methacrylic monomers, acrylonitrile, acrylamide and its derivatives, vinylpyrrolidinone or a mixture of at least two above mentioned monomers.

4. The method of claim 3 wherein the acrylic monomer is selected from the group consisting of acrylic acid or alkyl acrylates and mixtures thereof; and the methacrylic monomer is selected from the group consisting of methacrylic acid or alkyl methacrylates and mixtures thereof.

5. The method of claim 1 wherein said method forms allyl 2-[N-tert-butyl-N-(1-diethoxyphosphoryl-2,2-dimethylpropyl)aminoxy]propionate:

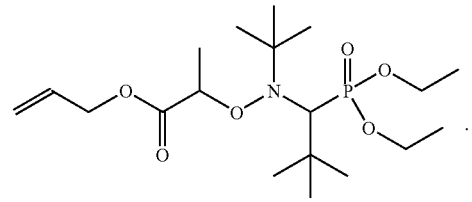

6. The method of claim 1 wherein said method forms N-allyl-2-[N-tert-butyl-N -(1-diethoxyphosphoryl-2,2-dimethylpropyl)aminoxy]propionamide:

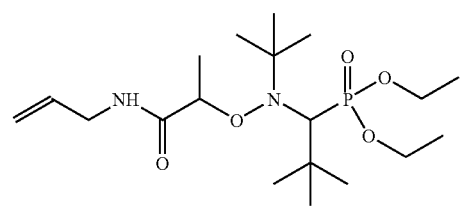

7. The method of claim 1 wherein said method forms a dialkoxyamine of formula:

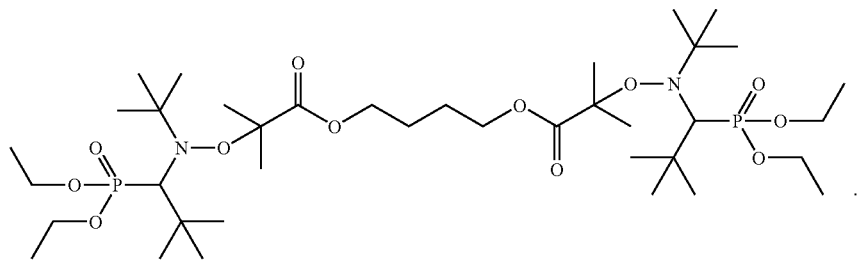
8. The method of claim 1 wherein said method forms a compound of formula (II) in which x=1, n=0, R=CH₃ and Z=CH₃(OCH₂CH₂)$_p$O—.
9. The method of claim 1 wherein Z is selected from the group consisting of CH₂=CH—CH₂—O—, CH₂=CH—CH₂—NH—, CH₃—(OCH₂CH₂)$_p$—O—, and —O—(CH₂)$_q$—O—, wherein p and q are independently integers at least equal to one.
* * * * *